(12) United States Patent
Dries et al.

(10) Patent No.: US 9,767,594 B2
(45) Date of Patent: Sep. 19, 2017

(54) IMAGE PROCESSING APPARATUS

(71) Applicant: KONINKLIJKE PHILIPS N.V., Eindhoven (NL)

(72) Inventors: Sebastian Peter Michael Dries, Hamburg (DE); Thomas Netsch, Hamburg (DE); Fabian Wenzel, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/371,182

(22) PCT Filed: Jan. 10, 2013

(86) PCT No.: PCT/IB2013/050210
§ 371 (c)(1),
(2) Date: Jul. 9, 2014

(87) PCT Pub. No.: WO2013/105042
PCT Pub. Date: Jul. 18, 2013

(65) Prior Publication Data
US 2015/0015570 A1 Jan. 15, 2015

Related U.S. Application Data

(60) Provisional application No. 61/584,844, filed on Jan. 10, 2012.

(51) Int. Cl.
*G06T 15/00* (2011.01)
*G06T 19/00* (2011.01)
(Continued)

(52) U.S. Cl.
CPC ............ *G06T 15/00* (2013.01); *G06F 19/321* (2013.01); *G06T 7/0012* (2013.01);
(Continued)

(58) Field of Classification Search
CPC .............. G06F 19/321; G06F 19/3437; G06F 19/3406; G06F 19/3487; G06F 19/345;
(Continued)

(56) References Cited

U.S. PATENT DOCUMENTS

| 5,622,170 | A | 4/1997 | Schulz |
| 5,740,802 | A | 4/1998 | Nafis et al. |
| 7,197,170 | B2 * | 3/2007 | Dwyer et al. ................ 382/128 |
| 8,630,467 | B2 | 1/2014 | Masumoto |
| 2004/0109032 | A1 | 6/2004 | Kim et al. |
| 2007/0244369 | A1 | 10/2007 | Gerard et al. |
| 2008/0074422 | A1 | 3/2008 | Dekel et al. |
| 2009/0079738 | A1 * | 3/2009 | Liao ............................ 345/427 |
| 2011/0141140 | A1 | 6/2011 | Duhamel et al. |
| 2011/0161854 | A1 | 6/2011 | Shukla |

(Continued)

FOREIGN PATENT DOCUMENTS

JP       2004089599 A       3/2004

OTHER PUBLICATIONS

Teistler, M. "Explore in 3D: a new virtual image navigation tool". SPIE Newsroom, Reference No. 10.1117/2.1200607.0222. http://spie.org/documents.Newsroom/Imported/22212006070222.pdf.

(Continued)

*Primary Examiner* — Jeffrey Chow

(57) ABSTRACT

Image processing apparatus 110 for processing a medical image, comprising an input 120 for obtaining the medical image 122 and medical data 124, the medical image constituting a field of view in three-dimensional [3D] patient data, and the medical data showing an anatomical context of a content of the field of view, an output 130 for providing an output image 160 comprising the medical image and a visualization of the medical data, the medical data constituting non-patient specific medical data, and the imaging processing apparatus further comprising a processor 140 for (i) performing an image alignment between the medical image and the medical data for obtaining a transformation providing a position of the content with respect to its anatomical context, and (ii) using the transformation for establishing a graphical representation of the field of view in the visualization of the medical data at said position.

20 Claims, 4 Drawing Sheets

(51) Int. Cl.
*G06F 19/00* (2011.01)
*G06T 7/00* (2017.01)

(52) U.S. Cl.
CPC ............ *G06T 7/0024* (2013.01); *G06T 19/00* (2013.01); *G06T 2207/30061* (2013.01); *G06T 2210/41* (2013.01); *G06T 2219/008* (2013.01)

(58) Field of Classification Search
CPC ..... G06F 19/322; G06F 17/50; G06T 7/0012; G06T 2207/10081; G06T 7/0081; G06T 2207/30004; G06T 2207/10072; G06T 15/08; G06T 2210/41; G06T 19/00; G06T 17/00; G06T 2207/10136; G06T 19/20; G06T 2219/2012; G06T 7/0032; G06T 7/0044; G06T 7/0046; G06T 15/00
See application file for complete search history.

(56) References Cited

U.S. PATENT DOCUMENTS

| | | |
|---|---|---|
| 2011/0172516 A1 | 7/2011 | Sugiura |
| 2011/0236868 A1 | 9/2011 | Bronstein et al. |
| 2015/0015570 A1 | 1/2015 | Dries et al. |

OTHER PUBLICATIONS

Maintz, J.B.A. et al. "An Overview of Medical Image Registration Methods". UU-CS-1998-22, Aug. 1998.

\* cited by examiner

IMAGE PROCESSING APPARATUS

This application is a national stage application under 35 U.S.C. §371 of International Application No. PCT/IB2013/050210 filed on Jan. 10, 2013 and published in the English language on Jul. 18, 2013 as International Publication No. WO/2013/105042, which claims priority to U.S. Application No. 61/584,844 filed on Jan. 10, 2012, the entire disclosures of which are incorporated herein by reference.

FIELD OF THE INVENTION

The invention relates to an image processing apparatus and a method of processing a medical image. The invention further relates to a workstation and an imaging apparatus comprising the image processing apparatus set forth, and to a computer program product for causing a processor system to perform the method set forth.

In the fields of medical image evaluation and medical image display, it may be desirable, when viewing a medical image constituting a field of view in three-dimensional [3D] patient data, to obtain an anatomical context of the content of said field of view.

BACKGROUND OF THE INVENTION

It is known to display, next to a medical image constituting a slice through 3D patient data, also a visualization of the 3D patient data comprising a cutting plane for graphically representing a position of the slice with respect to the 3D patient data.

For example, an article titled "Explore in 3D: a new virtual image navigation tool" by Michael Teistler, SPIE Newsroom, Reference number 10.11172.1200607.0222, as obtained from http://spie.org/documents/Newsroom/Imported/222/2006070222.pdf on 7 Dec. 2011, discloses a system allowing users to explore volumetric imaging data. FIG. 1 shows a volume data set being displayed on a display, titled "3D view" in FIG. 1. On an adjacent display, a slice through the volume data set is displayed, titled "2D view" in FIG. 1. The "3D view" further shows a cutting plane graphically representing said slice.

A problem of the aforementioned system is that it is not suitable for enabling a user to easily obtain an anatomical context of the slice.

SUMMARY OF THE INVENTION

It would be advantageous to have an apparatus or method enabling a user to more easily obtain an anatomical context of a medical image.

To better address this concern, a first aspect of the invention provides an image processing apparatus for processing a medical image, comprising an input for obtaining the medical image and medical data, the medical image constituting a field of view in three-dimensional [3D] patient data, and the medical data showing an anatomical context of a content of the field of view, an output for providing an output image comprising the medical image and a visualization of the medical data, the medical data constituting non-patient specific medical data, and the imaging processing apparatus further comprising a processor for (i) performing an image alignment between the medical image and the medical data for obtaining a transformation providing a position of the content with respect to its anatomical context, and (ii) using the transformation for establishing a graphical representation of the field of view in the visualization of the medical data at said position.

In a further aspect of the invention, a workstation and an imaging apparatus are provided comprising the image processing apparatus set forth.

In a further aspect of the invention, a method is provided for processing a medical image, comprising obtaining the medical image and medical data, the medical image constituting a field of view in three-dimensional [3D] patient data, and the medical data showing an anatomical context of a content of the field of view, providing an output image comprising the medical image and a visualization of the medical data, the medical data constituting non-patient specific medical data, and the method further comprising performing an image alignment between the medical image and the medical data for obtaining a transformation providing a position of the content with respect to its anatomical context, and using the transformation for establishing a graphical representation of the field of view in the visualization of the medical data at said position.

In a further aspect of the invention, a computer program product comprises instructions for causing a processor system to perform the method set forth.

The input obtains a medical image which constitutes a field of view in 3D patient data. The term field of view refers to an extent to which the 3D patient data is visible in the medical image, and typically corresponds to a portion of the 3D patient data. The content of the field of view, i.e., what is shown in the field of view, may be a body part, an organ, a part of the organ, a tissue, etc. The input further obtains medical data which provides an anatomical context of the content of the field of view. Thus, the medical data allows the content to be placed within a greater anatomy. For example, the content may be a part of an organ, and the medical data may provide the entire organ as the anatomical context. Similarly, the content may be a body part, and the medical data may provide an entire body as the anatomical context. The output provides an output image in which the medical image is shown as well as a visualization of the medical data. The output image thus shows the content of the field of view as well as separately the anatomical context of the content. A user can view both simultaneously by viewing the output image on a display.

The medical data constitutes non-patient specific medical data. Therefore, whereas the field of view of the medical image shows content of a particular patient, the medical data is non-patient specific. For example, the medical data may be a medical atlas showing a reference human body, thereby omitting any patient-specific details or variations. As a consequence, the anatomical context is a non-patient specific context, i.e., it differs from the anatomical context that is or may be provided by the 3D patient data itself.

The processor obtains a transformation that provides a position of the content with respect to the anatomical context shown in the medical data. The transformation may take the form of a transformation matrix, as known from the field of linear algebra, or a transformation function, and enables the processor to position the content of the field of view at an anatomically correct position within the medical data anatomical context.

For obtaining the transformation, the processor performs an image alignment which matches the medical image to the medical data. Image alignment is known per se from the field of image alignment, and may involve matching image structures, e.g., edges or corners in the medical image, to similar image structures in the medical data. Similarly, image alignment may involve matching landmarks, e.g., automatically or manually annotated points in the medical image, to corresponding landmarks in the medical data. It is noted that image alignment is frequently also referred to as image registration. A published report "An Overview of Medical Image Registration Methods" by J. B. A. Maintz et al., UU-CS-1998-22, August 1998, describes various techniques that may be advantageously used.

The processor uses the transformation to generate a graphical representation of the field of view in the visualization of the medical data at said position. As a result, the field of view in the 3D patient data, as is shown by the medical image, is graphically illustrated in the visualization of the medical data in the output image. Moreover, the graphical representation inherently also reflects and thus visualizes a position of the content of the field of view with respect to the anatomical context in the medical data.

By using medical data constituting non-patient specific medical data, the user is provided with a visualization in the output image that omits patient-specific details or variations. By obtaining a transformation between the medical image and the medical data, the content of the field of view of a particular patient can nevertheless be placed in the non-patient specific anatomical context. Finally, by establishing a graphical representation of the field of view in the visualization of the medical data, a position of the field of view, and thus of its content, is visualized within the non-patient specific anatomical context.

The invention is partially based on the recognition that it is convenient for a user to obtain an anatomical context when viewing a medical image of 3D patient data, but that 3D patient data is typically unsuitable for providing said anatomical context.

A reason for this is that 3D patient data typically contains patient specific details or variations, which may confuse or distract the user. Moreover, 3D patient data may, by its nature, be intended for medical diagnosis by a clinician, and hence be unsuitable for, e.g., a non-expert user. For example, the 3D patient data may contain too much detail, lack clearly defined structures, etc. A user may therefore fail to recognize the anatomical context provided by the 3D patient data. The present invention uses medical data that provides a non-patient specific anatomical context for the content of the field of view. The medical data therefore omits patient-specific details or variations. As a result, a user can easily learn or obtain the anatomical context from the output image. It is noted that also an expert user benefits from being able to easily learn or obtain the anatomical context.

Advantageously, the medical data may be specifically optimized for easy viewing by a non-expert user, as the medical data does not need to be used for medical diagnosis. Hence, the output image can simultaneously show an actual content of the field of view to the user, e.g., a broken bone or a malignant growth, as well as its anatomical context in an easy and understandable manner by means of the medical data. Advantageously, the user may more easily understand the medical image. Advantageously, a clinician may need less or no explanation of the anatomical context of said content.

Optionally, the processor is arranged for establishing the graphical representation as a surface intersecting the visualization of the medical data at said position. A surface is well suited for graphically representing the field of view provided by a medical image, as the field of view of the medical image is typically predominantly defined by the width and height of the field of view, rather than having a depth. For example, when the medical image corresponds to a slice through the 3D patient data, the field of view provided by the medical image extends predominantly along the width and height of the slice, with the depth being limited to the slice thickness, i.e., being typically thin. The field of view may therefore not extend significantly out of the medical image plane. A surface visually resembles said field of view, and thus provides a well-fitting graphical representation.

Optionally, the field of view extends along a depth in the 3D patient data, and the processor is arranged for (i) obtaining the depth and (ii) establishing a thickness of the surface in the visualization of the medical data for visualizing said depth. The field of view may have a certain depth. For example, a slice may have a slice thickness, which may be typically thin but in some situations may be thick. By establishing a thickness of the surface based on the depth of the field of view, said depth of the field of view is visualized. Advantageously, a more accurate graphical representation of the field of view is obtained.

Optionally, the medical image is a DICOM-encoded medical image, and the processor is arranged for obtaining the depth based on a DICOM data element of the DICOM-encoded medical image. DICOM, short for Digital Imaging and COmmunications in Medicine, is a standard for handling, storing, printing, and transmitting information in medical imaging. A DICOM data element may provide direct information on, or may be indicative of, the depth of the field of view. For example, a DICOM data element may comprise a slice thickness. A DICOM data element may also be indicative of the type of medical image, e.g., a cardiac or a brain image, with the type of medical image being indicative of said depth. The processor exploits this information by establishing the depth of the field of view based on the DICOM data element.

Optionally, the medical image is one of a plurality of medical images together constituting a medical volume, the medical volume providing a further field of view in the 3D patient data, and wherein the processor is arranged for using the transformation for establishing a further graphical representation of the further field of view in the visualization of the medical data. The plurality of medical images together provides a further field of view in the 3D patient data. Inherently, the further field of view encompasses the field of view provided by the medical image, as the medical image is one of the plurality of medical images. The processor uses the transformation to establish a further graphical representation of the further field of view in the visualization of the medical data. The user is thus provided with a visualization of the further field of view within the anatomical context of the medical data. Advantageously, a user may easily learn or obtain the anatomical context of the further field of view. Moreover, the user is provided with a visualization of a relative position of the field of view with respect to the further field of view. Advantageously, a user may easily learn said relative position by comparing the graphical representation with the further graphical representation in the output image.

Optionally, the processor is arranged for performing the image alignment between the medical volume and the medical data for obtaining the transformation. The medical volume provides a larger field of view than the field of view of only the medical image. Performing the image alignment is therefore facilitated, as a larger field of view provides more information that may be used by the image alignment. Advantageously, a larger field of view allows the medical volume to be more uniquely matched to the medical data compared to the image alignment matching only the medical image. Advantageously, occurrences of erroneous image alignment due to ambiguities in the matching are reduced. Advantageously, a more accurate transformation is obtained.

Optionally, the processor is arranged for establishing the further graphical representation, which is block-shaped, in the visualization of the medical data. The further field of view provided by the medical volume is typically block-shaped, for example, when the medical volume is defined by a plurality of adjacent, parallel slices in the 3D patient data. Here, the further field of view may be defined by the width and height of each of the plurality of slices and a distance between said slices, in particular the distance between a first and a last one of said slices. By establishing the further graphical representation having a block shape, a further graphical representation is obtained that reflects the further field of view typically provided by the medical volume. Advantageously, the block shape is easily established by applying a transformation to an initial block shape defined in the coordinate system of the medical volume for obtaining a block shape in the coordinate system of the medical data.

Optionally, the processor is arranged for (i) obtaining a non-angle preserving transformation between the medical volume and the medical data, and (ii) using the non-angle preserving transformation to deform the medical data for establishing the medical data in the block shape as corresponding to the further field of view. An angle-preserving linear transformation, also known as a conformal map in the field of mathematics, may be unsuitable or insufficient for mapping the medical volume to the medical data. For example, when the medical data shows a human body, an orientation of body parts may locally differ from that of the 3D patient data. For example, the patient may have differently positioned arms in the 3D patient data than the human body in the medical data. By taking said non-angle preserving aspects of the transformation into account in the image alignment, a non-angle preserving transformation is obtained, i.e., one that takes into account linear distortions such as shearing and perspective distortions as well as non-linear distortions.

The inventors have recognized that when the transformation comprises non-angle preserving components, an accurate graphical representation of the further field of view may have a non-block shape in the medical data. Said non-block shape may be difficult to interpret for a user. By using the non-angle preserving transformation to deform the medical data for establishing the medical data in the block shape as corresponding to the further field of view, the medical data is deformed such that the medical data in the aforementioned block shape corresponds to the further field of view of the medical volume. Therefore, the block shape remains an accurate representation of the field of view in the medical data. Advantageously, a user is not confused by the further field of view being represented by a non-block shape in the visualization of the medical data.

Optionally, the processor is arranged for (i) obtaining a non-angle preserving transformation between the medical volume and the medical data, and (ii) using the non-angle preserving transformation to reformat the plurality of medical images for establishing the further field of view as corresponding to the medical data in the block shape. The inventors have recognized that, instead of deforming the medical data such that the medical data in the aforementioned block shape corresponds to the further field of view of the medical volume, the non-angle preserving transformation may be used to reformat the medical volume so as to correspond to the medical data in the block shape. Hence, a reformatted medical volume is obtained. Advantageously, a user is not confused by the further field of view being represented by a non-block shape in the visualization of the medical data.

Optionally, the medical image is a DICOM-encoded medical image, and the processor is arranged for using a DICOM data element of the DICOM-encoded medical image for initializing and/or optimizing the image alignment. DICOM data elements may be advantageously used in performing the image alignment, as they provide information of the anatomical context of the medical image, e.g., which type of content is shown within the field of view. Hence, obtaining the transformation that places the content with respect to its anatomical context is facilitated. Advantageously, the image alignment is more accurate.

Optionally, the workstation set forth comprises a display for displaying the output image and a user input for enabling the user to navigate through the 3D patient data by modifying the field of view in the 3D patient data, and the processor is arranged for updating the graphical representation of the field of view, based on said modifying. The user is therefore continuously, i.e., during said navigation, provided with a position of the content of the current field of view with respect to its anatomical context. Advantageously, navigating through the 3D patient data is more convenient for a user.

It will be appreciated by those skilled in the art that two or more of the above-mentioned embodiments, implementations, and/or aspects of the invention may be combined in any way deemed useful.

Modifications and variations of the workstation, the imaging apparatus, the method, and/or the computer program product, which correspond to the described modifications and variations of the image processing apparatus, can be carried out by a person skilled in the art on the basis of the present description.

A person skilled in the art will appreciate that the method may be applied to multi-dimensional image data, e.g. to two-dimensional (2-D), three-dimensional (3-D) or four-dimensional (4-D) images. A dimension of the multi-dimensional image data may relate to time. For example, a three-dimensional image may comprise a time domain series of two-dimensional images. The image may be a medical image, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1:
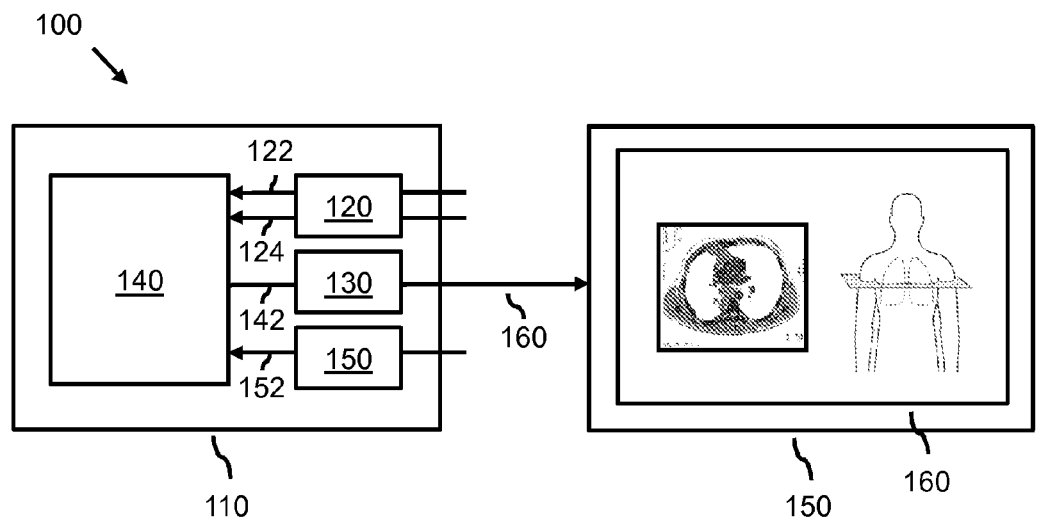
FIG. 1 shows an image processing apparatus according to the present invention connected to a display for displaying an output image.

FIG. 1 shows an image processing apparatus 110, henceforth referred to as apparatus 110, for processing a medical image 122. The apparatus 110 comprises an input 120 for obtaining the medical image 122 and medical data 124. The apparatus 110 further comprises an output 130 for providing an output image 160 comprising the medical image 122 and a visualization of the medical data 124. The apparatus 110 further comprises a processor 140 for performing an image alignment between the medical image 122 and the medical data 124, and for establishing a graphical representation in the visualization of the medical data 124. The processor 140 is shown to receive the medical image 122 and the medical data 124 from the input 140. Moreover, the processor 140 is shown to be connected to the output 130 for providing visualization data 142 to the output 130. Here, the visualization data 142 may comprise or be the output image 160. In this case, the processor 140 may generate the output image 160. Alternatively, the visualization data 142 may relate to the graphical representation and the output 130 may be arranged for obtaining the output image 160 from elsewhere within the apparatus 110, e.g., from another processor.

The output 130 is shown to be connected to a display 150 for displaying the output image 160 on said display. The display 150 is shown to be an external display, i.e., not being part of the apparatus 110. Alternatively, the display 150 may be part of the apparatus 110. The apparatus 110 and the display 150 may be part of, or form, a workstation 100.

The apparatus 110 may further comprise a user input 150 for obtaining navigation data 152 from a user. For that purpose, the user input 150 may be connected to a user interface means (not shown in FIG. 1) such as a mouse, keyboard, touch screen, etc, for receiving navigation commands from the user via the user interface means.

Figure 2:
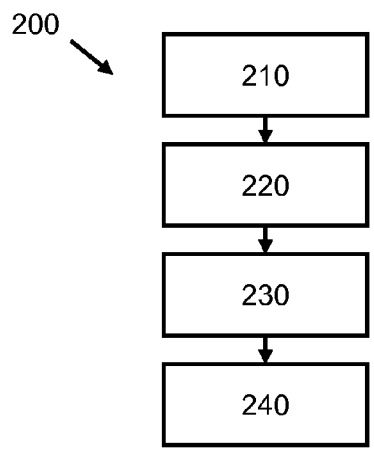
FIG. 2 shows a method according to the present invention.

FIG. 2 shows a method 200 for processing a medical image, comprising, in a first step titled "OBTAINING THE MEDICAL IMAGE AND IMAGE DATA", obtaining 210 the medical image and medical data, the medical image constituting a field of view in three-dimensional [3D] patient data, and the medical data showing an anatomical context of a content of the field of view. The method 200 further comprises, in a second step titled "PROVIDING AN OUTPUT IMAGE", providing 220 an output image comprising the medical image and a visualization of the medical data. The medical data constitutes non-patient specific medical data. The method 200 further comprises, in a third step titled "PERFORMING AN IMAGE ALIGNMENT", performing 230 an image alignment between the medical image and the medical data for obtaining a transformation providing a position of the content with respect to its anatomical context. The method 200 further comprises, in a fourth step titled "ESTABLISHING A GRAPHICAL REPRESENTATION", using the transformation for establishing 240 a graphical representation of the field of view in the visualization of the medical data at said position. It is noted that the above steps of the method 200 may be performed in any suitable order. In particular, the second step of providing 220 the output image may be performed last as part of the method 200.

The method 200 may correspond to an operation of the apparatus 110, and henceforth will be further discussed in reference to said operation of the apparatus 110. It is noted, however, that the method 200 may also be performed in separation of said apparatus 110, e.g., using a different image processing apparatus or a workstation.

Figure 3:
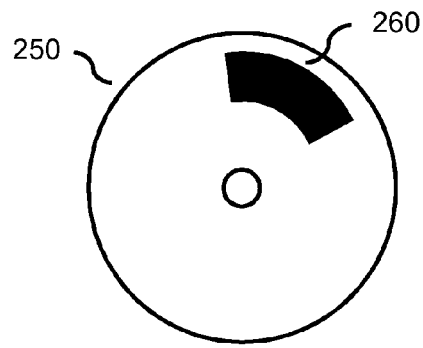
FIG. 3 shows a computer program product according to the present invention.

FIG. 3 shows a computer program product 260 comprising instructions for causing a processor system to perform the method according to the present invention. The computer program product 260 may be comprised on a computer readable medium 250, for example in the form of a series of machine readable physical marks and/or as a series of elements having different electrical, e.g., magnetic, or optical properties or values.

Figure 4A:
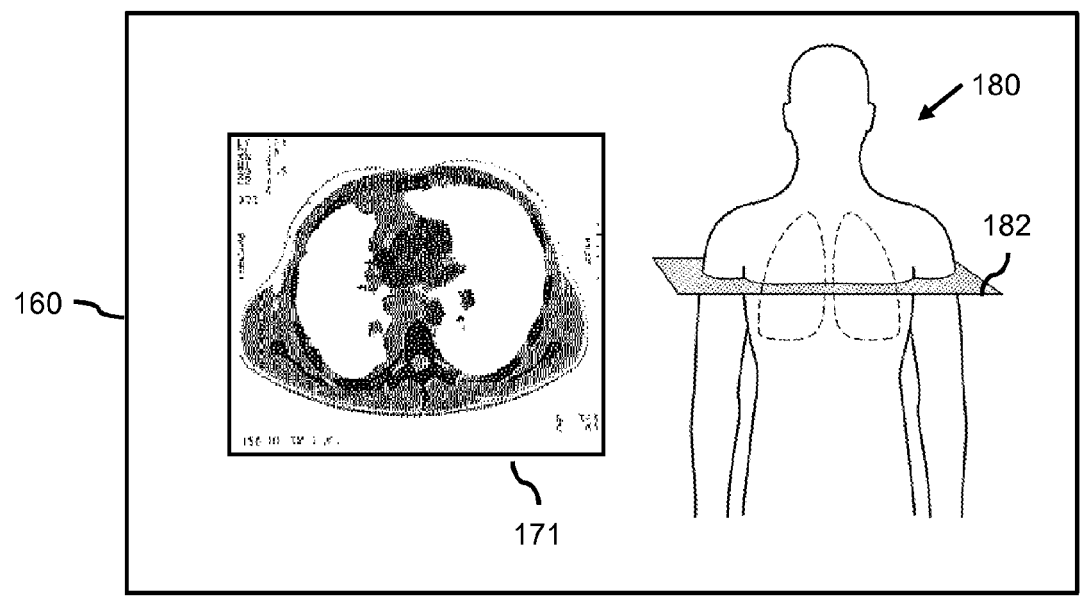
FIG. 4*a* shows a medical image and a visualization of medical data, said visualization comprising a graphical representation of a field of view of the medical image.

The operation of the apparatus 110, as well as optional aspects thereof, will be explained in reference to FIGS. 4a through 5b. FIG. 4a shows the output image 160. The output image 160 comprises a medical image 171 constituting a field of view in 3D patient data. In this example, the medical image 171 is shown to be an axial slice through 3D patient data comprising an upper body of the patient. As a result, the medical image 171 shows, as part of its field of view in the upper body of the patient, a part of the patient's lungs. The content of the field of view provided by the medical image 171 thus is a part of the patient's lungs.

In addition, the output image 160 comprises a visualization of medical data 180. The medical data differs from the 3D patient data in that the medical data constitutes non-patient specific medical data, i.e., is neither of the same patient as the 3D patient data nor any other specific patient. The medical data shows an anatomical context of the content of the field of view. In the example of FIGS. 4a-5b, the medical data shows a schematic representation of a human upper body as may be obtained from a medical atlas, in which individual organs are easily identifiable yet various details have been omitted for sake of clarity. The medical data thus provides anatomical context for the part of the patient's lungs.

The medical data has been visualized in the output image 160, i.e., the output image 160 comprises a visualization of said medical data. Here, the term visualization refers to all manners of depicting the medical data in the output image. Depending on the type of medical data, visualization may involve 3D rendering, e.g., when the medical data is 3D graphics data comprised of vertices, edges, etc. Alternatively, visualization may involve volume rendering, e.g., when the medical data is 3D volumetric data. Alternatively, visualization may involve simply drawing or directly inserting the medical data in the output image 160, e.g., when the medical data comprises an image or a drawing.

FIG. 4a shows a result of the processor 140 being arranged for performing an image alignment between the medical image 171 and the medical data to obtain a transformation providing a position of the content of the field of view with respect to its anatomical context. As a result, the part of the lungs shown in the medical image 171 is matched to a corresponding part of the upper body shown in the medical data. Moreover, the processor 140 is arranged for using the transformation to establish a graphical representation 182 of the field of view in the visualization of the medical data 180 at said position.

The graphical representation 182 is shown in FIG. 4a to be a surface 182 intersecting the visualization of the medical data 180 at the aforementioned position. The surface 182 therefore intersects the upper body through the part of the upper body that corresponds to the part of the lungs shown in the medical image 171. Here, the term corresponds refers to being an anatomically or computationally closest match.

As a result, the surface 182 visualizes the field of view provided by the medical image 171, in that a position as well as an extent of the field of view is graphically represented by the surface 182. The term extent here refers to a width and a height of the field of view, which is graphically represented by a corresponding width and height of the surface 182. The user can thus gather, from the surface 182 in the visualization of the medical data 180, the position and the width and the height of the field of view with respect to the medical data. The surface 182 may also graphically represent a depth of the field of view, i.e., the extent of the field of view in a direction that is perpendicular to the medical image surface. In FIG. 4a, the thickness of the surface 182 is shown to be limited, i.e., the surface 182 is a thin surface. This may be the result of the depth of the field of view being equally thin. Alternatively, this may be the result of the surface 182 not graphically representing said depth of the field of view. Also, this may be the result of the surface 182 not graphically representing the extent of the field of view at all, i.e., neither its width, height nor depth. Rather, the surface 182 may solely graphically represent the position of the field of view.

Figure 4B:
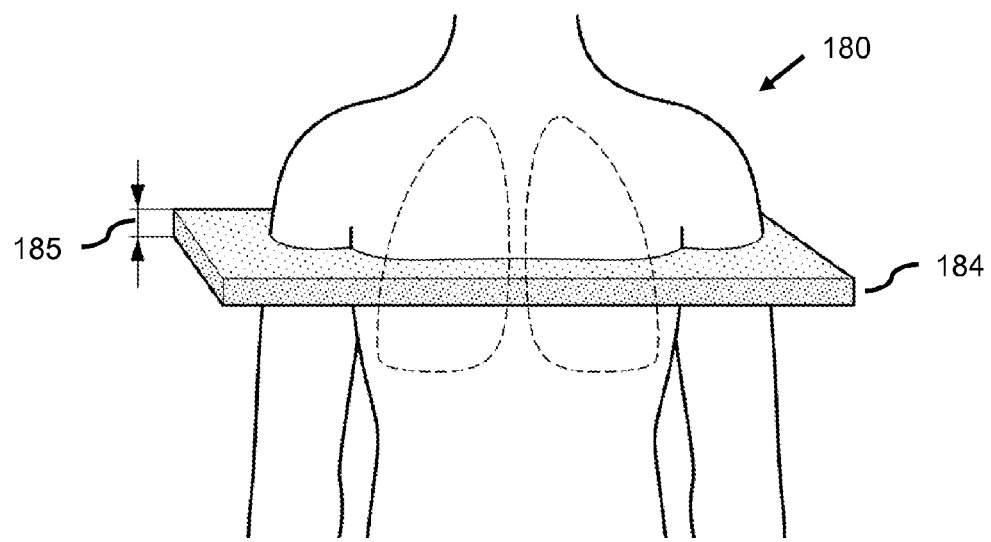
FIG. 4b shows the graphical representation, being a surface having a thickness.

FIG. 4b shows a cut-out version of the visualization of the medical data 180. Here, a result is shown of the field of view extending along a depth in the 3D patient data, and the processor 140 being arranged for (i) obtaining the depth and (ii) establishing a thickness 185 of the surface 184 in the visualization of the medical data 180 for visualizing said depth. In this example, the field of view may extend in the aforementioned depth direction in the 3D patient data. For example, the medical image 171 may represent a slice through the 3D patient data having a certain slice thickness. Hence, the depth of the field of view may correspond to the slice thickness. The processor 140 then visualizes said slice thickness by establishing the thickness 185 of the surface 184 accordingly. Obtaining said depth, e.g., the slice thickness, may involve, when the medical image 171 is a DICOM-encoded medical image, obtaining the depth based on, or directly from, a DICOM data element of the DICOM-encoded medical image. Said DICOM data element may be indicative of the depth of the field of view, e.g., the DICOM data element may directly comprise the aforementioned slice thickness.

It will be appreciated that the graphical representation of the field of view may take any other suitable form. For example, instead of being shown as a solid or opaque surface 182, as shown in FIG. 4a, the surface may be partially translucent or transparent. Instead of a surface, only an outline of a surface may be shown, e.g., indicating a width and a height of the field of view. The graphical representation may also involve a modification of the medical data, e.g., increase the brightness of a portion of the medical data. Hence, said portion of the medical data may constitute the graphical representation of the field of view. The graphical representation may also be a symbol, e.g., a camera symbol facing a portion of the medical data that corresponds to the field of view of the medical image 171.

Figure 5A:
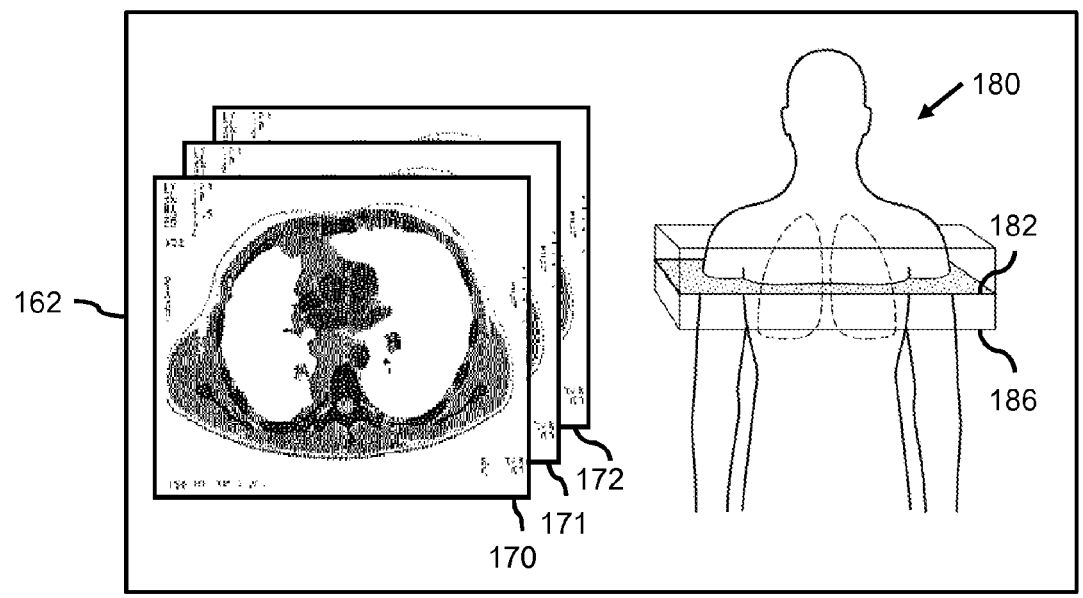
FIG. 5a shows a plurality of medical images and a further graphical representation of a further field of view provided by said medical images.

FIG. 5a shows an optional aspect of the present invention. Here, the medical image 171 is one of a plurality of medical images 170-172 together constituting a medical volume 170-172, with the medical volume 170-172 providing a further field of view in the 3D patient data. The plurality of medical images may, e.g., correspond to a series of slices through the 3D patient data. The processor 140 may be arranged for using the transformation to establish a further graphical representation 186 of the further field of view in the visualization of the medical data 180. For that purpose, the processor 140 may be arranged for performing the image alignment between the medical volume 170-172 and the medical data for obtaining the transformation. Alternatively, the processor 140 may perform the image alignment between one of the plurality of medical images 170-172 and the medical data, and may apply said transformation to the others of said medical images 170-172.

FIG. 5a shows the further graphical representation 186 of the further field of view having a block shape, i.e., being a wireframe block or slab. Said shape may be the result of the further field of view also having a block shape within the 3D patient data. For example, when the plurality of medical images 170-172 are a plurality of adjacent, parallel slices through the 3D patient data, said further field of view may be block-shaped. Hence, the further graphical representation 186 may graphically represent a width, a height and a depth of the further field of view due to a width, height and depth of the wireframe block 186 being chosen accordingly. It is noted, however, that the further graphical representation 186 may take any other suitable form. For example, the further graphical representation 186 may comprise a plurality of surfaces, with each of the plurality of surfaces graphically representing a field of view of a respective one of the plurality of medical images 170-172.

In addition to the further graphical representation 186, i.e., the wireframe block, the surface 182 graphically representing the field of view of the medical image 171 is shown as well. From the relative positions of the surface 182 and the wireframe block 186, it can be seen that the field of view of the medical image 171 is located in the middle of the further field of view of the plurality of medical images 170-172, e.g., may be a middle slice. Said relative position of the surface 182 may correspond to a relative position of a currently shown medical image with respect to the plurality of medical images 170-172, i.e., the surface 182 being located in the middle of the wireframe block 186 may be indicative of the currently shown medical image being a middle one 171 of the plurality of medical images 170-172. It is noted that this is not shown in FIG. 5a, where, for sake of explanation, the plurality of medical images 170-172 are shown as a stack showing a first one 170 of the medical images on top instead of the middle one 171 of the medical images.

It is noted that various possibilities exist for establishing the further graphical representation 186 in the visualization of the medical data 180. For example, the processor 140 may be arranged for obtaining an angle-preserving transformation between the medical volume 170-172 and the medical data. An angle-preserving transformation may involve any or all of: rotation, scaling, or translation. For that purpose, the processor 140 may obtain an angle-preserving transformation matrix which is indicative of a transformation of a point in a coordinate system of the plurality of medical images 170-172 to a point in the coordinate system of the medical data, or of the visualization of the medical data 180. Such matrices, as well as other angle-preserving transformation functions, are known from the fields of image alignment and linear algebra. The processor 140 may be arranged for using the angle-preserving transformation for establishing the further graphical representation 186 having a block shape in the visualization of the medical data 180. As a result, the aforementioned wireframe block 186 may be obtained, as shown in FIG. 5a.

Figure 5B:
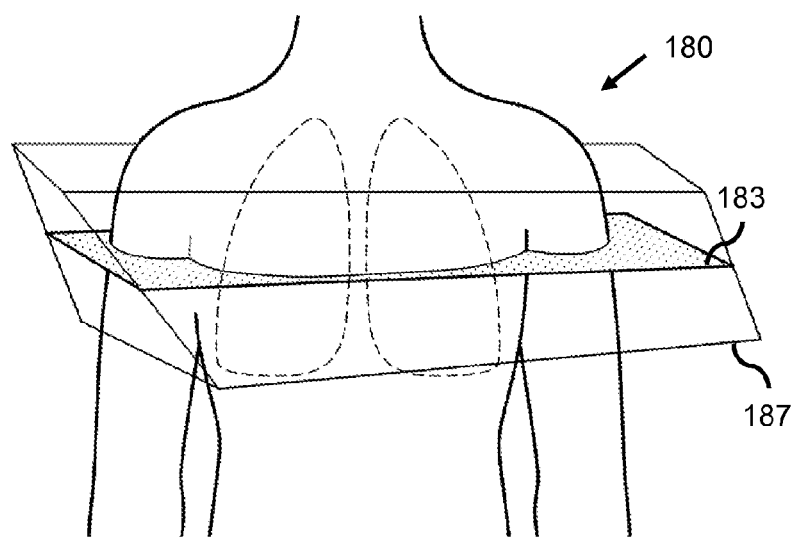
FIG. 5b shows the further graphical representation having a sheared non-block shape.

An accurate transformation between the medical volume 170-172 and the medical data may also comprise non-angle preserving components that take into account shearing, perspective distortions, and non-linear distortions. The transformation, as obtained by the processor, may therefore comprise said non-angle preserving components. A reason for said non-angle preserving components is that distortions of the medical data may exist with respect to the 3D patient data, e.g., due to patient-specific details or variations, or due to imaging related aspects. Thus, the transformation between the plurality of medical images 170-172 and the medical data may be a non-angle preserving transformation. The processor 140 may be arranged for obtaining the non-angle preserving transformation between the medical volume 170-172 and the medical data. The non-angle preserving transformation may take into account the aforementioned shearing, perspective distortions, non-linear distortions, etc, of the medical volume 170-172 with respect to the 3D medical data, or vice versa. The processor 140 may be arranged for using the non-angle preserving transformation to establish the further graphical representation 186 in the visualization of the medical data 180, e.g., by applying the non-angle preserving transformation to an initial block shape defined in the coordinate system of the medical volume 170-172. As a result, a non-block shape may be automatically obtained in the visualization of the medical data 180. A result of this is shown in FIG. 5b, where a sheared non-block shape 187 is shown as well as the surface 183. It is noted that when the non-angle preserving transformation also comprises non-linear components, the edges or lines of the block shape 187 may be transformed into curves. In the example of FIG. 5b, however, the transformation does not comprise non-linear components.

It is noted that the sheared non-block shape 187 may be difficult to interpret for a user. To avoid confusion of the user, the processor 140 may be arranged for disregarding the non-angle preserving components of the transformation in order to establish the further graphical representation having a block shape. In such a case, the further graphical representation does not accurately represent the further field of view, but confusion of a user due to the sheared non-block shape 187 may be avoided.

Figure 5C:
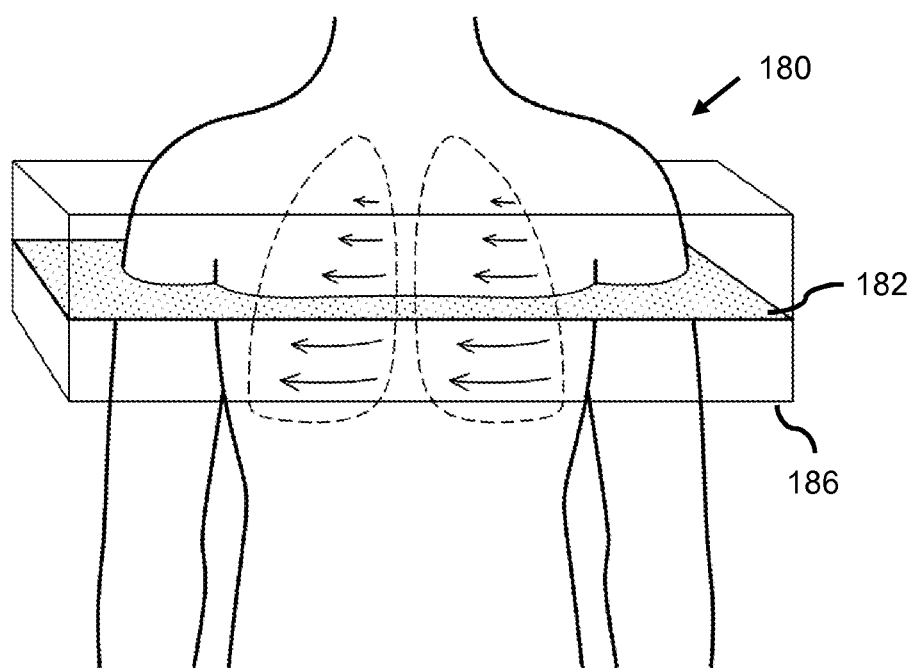
FIG. 5c shows the further graphical representation having a block shape and a result of the medical data being deformed.

Alternatively, the processor 140 may be arranged for using the non-angle preserving transformation to deform the medical data for establishing the medical data in the block shape 186 as corresponding to the further field of view. An example of this is shown in FIG. 5c, where the deformation of the medical data is schematically indicated by means of arrows. It is noted that in the example of FIG. 5c, the non-angle preserving transformation is assumed to obtain otherwise the sheared non-block shape 187 of FIG. 5b. Hence, the deformation of the medical data essentially corresponds to the deformation needed for deforming the sheared non-block shape 187 of FIG. 5b into the block shape 186 of FIG. 5c. Deforming the medical data may involve, e.g., adjusting coordinates of vertices when the medical data is 3D graphics data, or adjusting values or positions of voxels when the medical data is volumetric data. It is noted that such techniques are known per se from the fields of image alignment and image processing. As a result, the medical data in the block shape 186 corresponds to the further field of view after said deformation. Here, the term corresponds refers to being an anatomically or computationally close or closest match. Consequently, the block shape 186 provides an accurate graphical representation of the further field of view.

Alternatively, the processor 140 may be arranged for using the non-angle preserving transformation to reformat the plurality of medical images 170-172 for establishing the further field of view as corresponding to the medical data in the block shape 186. As a result, a new plurality of medical images is obtained, of which the further field of view corresponds to the medical data in the block shape 186. Consequently, the block shape 186 provides an accurate graphical representation of its further field of view. It is noted that reformatting techniques are known per se from the field of medical imaging. Reformatting may comprise generating a new plurality of slices intersecting the 3D patient data.

It is noted that the output image 160 may comprise a side-by-side visualization of the medical image 171 and the visualization of the medical data 180. The visualization may be interactive, i.e., the user may navigate through the 3D patient data, and as a result, a different medical image may be displayed. The different medical image may be a different one of the aforementioned plurality of medical images 170-172. The processor may be arranged for updating the graphical representation 182 of the field of view, based on the navigation. Hence, a change in field of view due to a change in medical image may result in a change in position and/or shape of the graphical representation 182 of the field of view. For enabling said navigation by the user, the apparatus 110 may comprise a user input 150, as shown in FIG. 1. Here, the apparatus 110 and the display 150 may be part of, or together form, a workstation 100 that enables the user to navigate through the 3D patient data.

In general, the graphical representation may be a planar surface. The graphical representation may also be a non-planar surface, e.g., a curved surface, when the transformation between medical image and medical data comprises non-linear components. The graphical representation may be based on computer graphics, i.e., may be comprised of vertices, edges, etc. The graphical representation may also be pixel-based or voxel-based. The further graphical representation may be a block shape such as a wireframe block or slab. The further graphical representation may also be a translucent or semi-translucent block.

The image alignment may be based on any suitable technique from the field of image alignment. In particular, multi-modality methods may be used to compensate for a difference in modality or type between the 3D patient data and the medical data. When the medical image is a DICOM-encoded medical image, the processor may be arranged for using a DICOM data element of the DICOM-encoded medical image for initializing and/or optimizing the image alignment. For example, angulations and positioning information may be used.

The 3D patient data may be from various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM). The 3D patient data may be part of 4D patient data. In the 4D patient data, a dimension may relate to time, e.g., the 4D patient data may be a time-series of 3D images. The plurality of medical images may together constitute the 3D patient data. For example, the plurality of medical images may be a plurality of slices, together constituting a medical volume as well as all of the 3D patient data. Alternatively, the medical volume, i.e., the plurality of medical images, may be a subset or a portion of the 3D patient data.

The medical data may be based on acquired medical data in which patient-specific details or variations have been removed, e.g., by averaging. The medical data may also be automatically or manually generated data, e.g., a 3D computer graphics model or a 2D drawing. In general the medical data may be 2D or 3D medical atlas data.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or to be used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. Image processing apparatus for processing a medical image, comprising:
   an input for obtaining the medical image and medical data, the medical image constituting a field of view in three-dimensional (3D) patient data, and the medical data showing an anatomical context of a content of the field of view;
   an output for concurrently displaying a first output image comprising the medical image and a second output image comprising a visualization of the medical data;
   the medical data constituting non-patient specific medical data; and
   the imaging processing apparatus further comprising a processor for (i) performing an image alignment between the medical image and the medical data for obtaining a transformation providing a position of the content with respect to its anatomical context, and (ii) using the transformation for establishing a graphical representation of the field of view in the visualization of the medical data at said position.

2. Image processing apparatus according to claim 1, wherein the processor is arranged for establishing the graphical representation as a surface intersecting the visualization of the medical data at said position.

3. Image processing apparatus according to claim 2, wherein the field of view extends along a depth in the 3D patient data, and the processor is arranged for (i) obtaining the depth and (ii) establishing a thickness of the surface in the visualization of the medical data for visualizing said depth.

4. Image processing apparatus according to claim 3, wherein the medical image is a DICOM-encoded medical image, and the processor is arranged for obtaining the depth, based on a DICOM data element of the DICOM-encoded medical image.

5. Image processing apparatus according to claim 1, wherein the medical image is one of a plurality of medical images together constituting a medical volume, the medical volume providing a further field of view in the 3D patient data, and wherein the processor is arranged for using the transformation for establishing a further graphical representation of the further field of view in the visualization of the medical data.

6. Image processing apparatus according to claim 5, wherein the processor is arranged for performing the image alignment between the medical volume and the medical data for obtaining the transformation.

7. Image processing apparatus according to claim 6, wherein the processor is arranged for establishing the further graphical representation having a block shape in the visualization of the medical data.

8. Image processing apparatus according to claim 7, wherein the processor is arranged for (i) obtaining a non-angle preserving transformation between the medical volume and the medical data, and (ii) using the non-angle preserving transformation to deform the medical data for establishing the medical data in the block shape as corresponding to the further field of view.

9. Image processing apparatus according to claim 7, wherein the processor is arranged for (i) obtaining a non-angle preserving transformation between the medical volume and the medical data, and (ii) using the non-angle preserving transformation to reformat the plurality of medical images) for establishing the further field of view as corresponding to the medical data in the block shape.

10. Image processing apparatus according to claim 1, wherein the medical image is a DICOM-encoded medical image, and the processor is arranged for using a DICOM data element of the DICOM-encoded medical image for initializing and/or optimizing the image alignment.

11. Workstation comprising the image processing apparatus of claim 1.

12. Workstation according to claim 11, comprising a display for displaying the output image and a user input for enabling the user to navigate through the 3D patient data by modifying the field of view in the 3D patient data, and wherein the processor is arranged for updating the graphical representation of the field of view, based on said modifying.

13. Imaging apparatus comprising the image processing apparatus of claim 1.

14. A method of processing a medical image, comprising:
obtaining the medical image and medical data, the medical image constituting a field of view in three-dimensional patient data, and the medical data showing an anatomical context of a content of the field of view;
concurrently displaying a first output image comprising the medical image and a second output image comprising a visualization of the medical data;
the medical data constituting non-patient specific medical data;
and the method further comprising performing an image alignment between the medical image and the medical data for obtaining a transformation providing a position of the content with respect to its anatomical context; and
using the transformation for establishing a graphical representation of the field of view in the visualization of the medical data at said position.

15. A non-transitory computer readable medium that includes a computer program product that, when executed by a processor system, causes the processor system to:
obtain a medical image and medical data, the medical image constituting a field of view in three-dimensional patient data, and the medical data showing an anatomical context of a content of the field of view based on non-patient specific medical data;
perform an image alignment between the medical image and the medical data to obtain a transformation providing a position of the content with respect to its anatomical context;
use the transformation to determine a graphical representation of the field of view in the visualization of the medical data at said position; and
concurrently display a first output image comprising the medical image and a second output image comprising a visualization of the medical data.

16. The medium of claim 15, wherein the graphical representation includes a surface that intersects the visualization of the medical data at said position.

17. The medium of claim 16, wherein the field of view extends along a depth in the 3D patient data, and the program causes the processor system to obtain the depth and establish a thickness of the surface in the visualization of the medical data for visualizing said depth.

18. The medium of claim 15, wherein the medical image is a DICOM-encoded medical image, and the program causes the processor system to use a DICOM data element of the DICOM-encoded medical image to initialize and/or optimize the image alignment.

19. The medium of claim 15, wherein the medical image is one of a plurality of medical images together constituting a medical volume, the medical volume providing a further field of view in the 3D patient data, and the program causes the processor system to perform an image alignment between the medical volume and the medical data to obtain the transformation.

20. The medium of claim 15, wherein the graphical representation includes a block shape in the visualization of the medical data.

* * * * *